United States Patent [19]

Naleway et al.

[11] Patent Number: 5,242,805
[45] Date of Patent: Sep. 7, 1993

[54] LONG WAVELENGTH LIPOPHILIC FLUOROGENIC GLYCOSIDASE SUBSTRATES

[75] Inventors: John J. Naleway; Yu-zhong Zhang; Richard P. Haugland, all of Eugene, Oreg.

[73] Assignee: Molecular Probes, Inc., Eugene, Oreg.

[21] Appl. No.: 749,255

[22] Filed: Aug. 23, 1991

[51] Int. Cl.$^5$ .................................................. C12Q 1/34
[52] U.S. Cl. ........................................... 435/18; 435/4; 536/123.13; 436/3; 436/35; 544/102
[58] Field of Search .................... 536/1.1; 544/102; 435/4, 18; 436/3, 35; 372/53

[56] References Cited

U.S. PATENT DOCUMENTS

| | | | |
|---|---|---|---|
| 3,731,222 | 5/1973 | Drexhage | 544/102 |
| 4,812,409 | 3/1989 | Babb et al. | 435/4.0 |

OTHER PUBLICATIONS

Legler & Liedtke, *Glucosylceramidase from Calf Spleen*, Biol. Chem. 366, 1113 (1985).

Nolan, et al., Fluorescence-activated cell analysis and sorting of viable mammalian cells based on β-D-galactosidase activity after transduction of *Escherichia coli* lacZ, Cell Biology 85, 2603 (1988).

(List continued on next page.)

*Primary Examiner*—Ronald W. Griffin
*Assistant Examiner*—Pamela S. Webber
*Attorney, Agent, or Firm*—Allegra J. Helfenstein

[57] ABSTRACT

The claimed invention relates to a substrate for evaluating glycosidic enzymes comprising a resorufin derivative of the general formula:

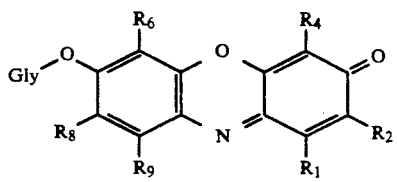

wherein Gly is a carbohydrate bonded to resorufin by a glycosidic linkage;

where at least one of substituents $R_1$, $R_2$, $R_4$, $R_6$, $R_8$, and $R_9$ is a lipophilic residue of the formula —L(CH$_2$)$_n$CH$_3$, where n is greater than 3 and less than 22, and where L is a methylene —CH$_2$—, an amide —NHCO—, a sulfonamide —NHSO$_2$—, a carboxamide —CONH—, a carboxylate ester —COO—, a urethane —NHCOO—, a urea —NHCONH—, or a thiourea —NHCSNH—; and where the remainder of substituents $R_1$, $R_2$, $R_4$, $R_6$, $R_8$, and $R_9$, which may be the same or different, are hydrogen, halogen, or other lipophilic residues, which may be the same or different, containing from about 1 to about 22 carbon atoms of the formula —L'(CH$_2$)$_m$CH$_3$, where m is less than 22, and where L' is a methylene —CH$_2$—, an amide —NHCO—, a sulfonamide —NHSO$_2$—, a carboxamide —CONH—, a carboxylate ester —COO—, a urethane —NHCOO—, a urea —NHCONH—, or a thiourea —NHCSNH—.

A preferred embodiment of the invention is a non-fluorescent substrate specifically hydrolyzable by a glycosidase inside a cell to yield, after greater than about 2 minutes, an orange to red fluorescent detection product which is retained inside a viable cell more than about 2 hours at greater than about 15° C. and which is non-toxic to the cell. The substrates are used for evaluating a glycosidic enzyme in living plant or animal cells whether the enzyme is present endogenously; present as a result of manipulation of the cell's genome, or added to the cell exogenously, such as by covalently binding the enzyme to a protein to form an enzyme-protein complex that enters the cell.

20 Claims, 2 Drawing Sheets

OTHER PUBLICATIONS

Ikenaka, et al., *Laboratory Methods: Reliable Transient Promoter Assay Using Fluorescein-di-β-D-galactopyranoside Substrate,* DNA & Cell Biol. 9, 279 (1990).

Hofman & Sernetz, *Immobilized Enzyme Kinetics Analyzed by Flow-Through Microfluorimetry,* Analytica Chimica Acta 163, 67 (1984).

Reiners, et al., *Fluorescence Assay for Per-Cell Estimation of Cytochrome P-450-Dependent Monooxygenase Activities in Keratinocyte Suspensions and Cultures,* Analyt. Biochem. 188, 317 at p. 322 (1990).

Jefferson, EMBO J 6, 3901 (1987).

Jefferson, *The Gus Reporter Gene System,* Nature 342, 837 (1989).

Jarvis, Hagen, & Sprague, *Identification of a DNA segment that is necessary and sufficient for α-specific gene control in Saccharomyces cerevisiae: implications for regulation of α-specific genes and a specific genes,* , Molec. & Cell. Biol. 8, 309 (1988).

David W. Galbraith, *Selection of Somatic Hybrid Cells by Fluorescence-Activated Cell Sorting,* in Cell Culture and Somatic Cell Genetics of Plants 1, 433, ch. 50 (1984).

Emilie, et al., Eur. J. Immunol. 19, 1619 (1989).

Enzyme Nomenclature, 1984, Int'l Union Biochemistry, Academic Press (1984) pp. 306–326.

LONG WAVELENGTH LIPOPHILIC FLUOROGENIC GLYCOSIDASE SUBSTRATES

This invention was made with Government support under grant GM 38987 awarded by the National Institutes of Health. The Government has certain rights in this invention.

FIELD OF THE INVENTION

This invention relates to reddish fluorogenic substrates used to analyze glycosidic enzyme activity. In particular, the invention relates to improved resorufin glycosides that incorporate a lipophilic group, useful in detecting cells producing enzymes that hydrolyze the glycoside.

BACKGROUND INFORMATION

By studying the chemical reactions that occur inside particular cells, scientists can learn more about those cells. It is difficult to conduct experiments inside cells, however. One technique shown to be useful is to develop a probe to enter the cell, react with a particular substance inside the cell, and signal that the reaction has occurred.

Unfortunately, many tests for the presence of products inside of cells are destructive to the cells being tested, either killing them outright or preventing them from growing or reproducing as normal cells. They may have other disadvantages as well. For example, radioactive substances, while sufficiently sensitive to distinguish cells, ultimately destroy the viability of the cells during measurement and destroy the reproductive capability of the cells. In addition, radioactive reagents are dangerous to handle and require slow and cumbersome experimental techniques and disposal methods, and radioactive measurements can not be done on viable cells. Dyes that are chromogenic rather than fluorescent, e.g., 5-bromo-4-chloroindolyl galactoside (X-gal) and 5-bromo-4-chloro-3-indolyl $\beta$-D-glucuronic acid (X-GlcU) are less sensitive and require a large turnover of substrate or multiple reactions to obtain a signal. Furthermore, the hydrolysis product of X-gal (and X-GlcU) is frequently toxic to cells.

In order to study living cells, tests are typically limited to only a portion of a cell population. If the subject cell population is a very small one, however, and some cells are removed for testing, sufficient cells may not be available for further study or use. In order to study or otherwise utilize a small population of cells, as living cells, it is essential to be able to locate and, if possible, separate those cells without destroying them.

Ideally, a probe used to identify and separate a living cell which contains a particular substance or to localize a substance in an organelle of a living cell, has the following characteristics: 1) the probe enters the cell without damaging the cell or preventing its subsequent cloning or reproduction, 2) the probe reacts exclusively with the particular substance inside the cell to form a specific detection product, 3) the detection product produces a signal sufficiently intense to distinguish the cell from other cells that do not contain the substance or that contain less of the substance, and 4) the detection product is sufficiently well retained by the cell to permit analysis and, if desired, sorting of the cell.

Fluorescent enzyme substrates generally make ideal probes. Often, a fluorescent substrate can enter the cell using the cell's own mechanisms. Once inside the cell, a fluorescent substrate usually only reacts with a specific enzyme. Typically, the reaction produces a change in fluorescence which is sufficiently distinctive to distinguish cells or organelles that have the enzyme from cells or organelles that do not or that have lower levels of the enzyme.

Use of fluorescent substrates also permits utilization of flow cytometers. Flow cytometers are designed for the rapid and specific sorting of highly fluorescent cells from cells that have low fluorescence. Flow cytometers commonly use an argon laser to excite the fluorescent product inside the cells. Thus, excitation of fluorescence at the principal wavelengths of the argon laser (488 or 514 nm) or by longer wavelength excitation sources is a preferred characteristic of a fluorescent substrate for some applications. As a result, fluorescent substrates which respond poorly at this wavelength, such as umbelliferone (7-hydroxycoumarin) conjugates, are not as suitable for such applications.

Two advantages exist for even longer wavelength probes that absorb at greater than about 500 nm: 1) the autofluorescence from cells generally decreases with increasing wavelengths and 2) longer wavelength emission can be detected in the presence of a second dye such as fluorescein that emits at a shorter wavelength, permitting measurement of two parameters that are detected simultaneously or sequentially at separate wavelengths.

Quantitative imaging of fluorescence using microscopes and image intensifiers has been used to measure substances such as intracellular calcium ions and superoxide production in living cells. Methods exist for quantitatively measuring changes in fluorescence intensity with time, such as occurs in turnover of fluorescent substrates. Quantitative differences in the fluorescence change that result from hydrolysis of a fluorescent substrate may be the result of either a higher enzyme content or a faster enzyme turnover rate.

Fluorescent substrates, and flow cytometry, can also be used to detect and separate cells which have acquired the ability to produce certain enzymes as a result of a gene fusion. Gene fusions are used to study or work with a particular gene or genetic material by inserting it into a host cell. Typically, the foreign genetic material is inserted into the host cell using a vector (transfection). Alternatively, the foreign genetic material enters the cell through pores created in the membrane, e.g. electroporation, or is microinjected into the host cell. Cells which have successfully incorporated the foreign genetic material are termed "transformed".

One way to determine whether transformation has occurred is to test for the presence of a protein product resulting from the inserted genetic material. Depending on the nature of the foreign genetic material inserted into the host cell and the desired genetic characteristics of the transformed cell, however, testing for successful transformation can be expensive and time-consuming.

Glycosidic enzymes are commonly used to differentiate cells, including transformed cells. For example, $\beta$-galactosidase is a bacterial enzyme commonly found in *Escherichia coli* (*E. coli*). The enzyme is coded by the *E. coli* lacZ gene. The presence of $\beta$-galactosidase activity in a transformed cell can be used to indicate the presence of the foreign lacZ gene. The lacZ gene, in turn, is used as a genetic marker to indicate that additional foreign genetic material, including the lacZ gene, has been incorporated into a host cell otherwise lacking in $\beta$-galactosidase. The enzyme $\beta$-glucuronidase, coded by the GUS gene in *E. coli*, is primarily used to detect transformation in plant cells and tissues, where this activity is normally lacking (Jefferson, *The GUS Reporter Gene System*, NATURE 342, 837 (1989)), but it is also useful in detecting transformations in mammalian cells.

Not all glycosidic enzymes are useful as marker enzymes. Some glycosidic enzymes, such as β-glucosidase, are intrinsically present in many cells. Their activity, however, may be characteristic of the cell type, of an organelle of the cell, or of the metabolic state of the cell. Some common glycosidic enzymes and representative carbohydrates cleaved by such enzymes are listed in Table 1. This listing is not meant to limit or define the extent of all glycosidic enzymes.

TABLE 1

SELECTED GLYCOSIDIC ENZYMES
(from ENZYME NOMENCLATURE, 1984 (International Union Biochemistry, Academic Press, 1984 pages 306–26)

| E.C. NO. | ENZYME | CARBOHYDRATE-GROUP SELECTIVITY |
|---|---|---|
| 3.2.1.18 | Sialidase | N- or O-Acetyl Neuraminic Acid (Sialic Acid) |
| 3.2.1.20 | α-Glucosidase | α-D-Glucose |
| 3.2.1.21 | β-Glucosidase | β-D-Glucose |
| 3.2.1.22 | α-Galactosidase | α-D-Galactose |
| 3.2.1.23 | β-Galactosidase | β-D-Galactose |
| 3.2.1.24 | α-Mannosidase | α-D-Mannose |
| 3.2.1.25 | β-Mannosidase | β-D-Mannose |
| 3.2.1.26 | β-Fructofuranosidase | β-D-Fructose |
| 3.2.1.30 | N-Acetyl-β-glucosaminidase | β-D-N-Acetyl-Glucosamine |
| 3.2.1.31 | β-Glucuronidase | β-D-Glucuronic Acid |
| 3.2.1.38 | β-D-Fucosidase | β-D-Fucose |
| 3.2.1.40 | α-L-Rhamnosidase | α-L-Rhamnose |
| 3.2.1.43 | β-L-Rhamnosidase | β-L-Rhamnose |
| 3.2.1.48 | Sucrose α-glucosidase | α-D-Glucose |
| 3.2.1.49 | α-N-Acetylgalactosaminidase | α-D-N-Acetyl-Galactosamine |
| 3.2.1.50 | α-N-Acetylglucosaminidase | α-D-N-Acetyl-Glucosamine |
| 3.2.1.51 | α-L-Fucosidase | α-L-Fucose |
| 3.2.1.52 | β-N-Acetylhexosaminidase | β-D-N-Acetyl-Glucosamine |
| 3.2.1.53 | β-N-Acetylgalactosaminidase | β-D-N-Acetyl-Galactosamine |
| 3.2.1.55 | α-L-Arabinofuranosidase | α-L-Arabinose |
| 3.2.1.76 | L-Iduronidase | α-L-Iduronic Acid |
| 3.2.1.85 | 6-Phospho-β-galactosidase | 6-Phospho-β-D-Galactose |
| 3.2.1.86 | 6-Phospho-β-glucosidase | 6-Phospho-β-D-Glucose |
| 3.2.1.88 | β-L-Arabinosidase | β-L-Arabinose |
| 3.2.1.4 | Cellulase | β-Cellobiose |

When the presence of an enzyme is used to indicate gene fusion, the marker included with the foreign genetic material provides a relatively fast and inexpensive means of detecting successful transformation. Cells which have successfully incorporated the marker gene are called "marker" positive (e.g. lacZ+ or GUS+). Using the marker gene to show successful transformation, however, requires detecting the activity of a very small number of enzyme molecules, usually in the cytosol of the lacZ+ or GUS+ cell. The activity must be detected in a way which does not inhibit further use, replication or study of the living transformed cell. Activity of the marker enzyme is most often used to monitor: 1) promotor and/or repressor effectiveness; 2) the crucial sequence of the promotor gene after sequential or selective deletions on it; 3) the level of induction of the operon so as to evaluate the effectiveness of potential inducer(s); and 4) any possible gene expression regulation at the pro- and/or post-transcription or translation level. Such monitoring is done by the methods generally known in the art, such as described by Jarvis, Hagen, & Sprague, *Identification of a DNA segment that is necessary and sufficient for α-specific gene control in Saccharomyces cerevisiae: implications for regulation of α-specific and a-specific genes*, MOLEC. & CELL. BIOL. 8, 309 (1988).

Several substrates derived from fluorescent dyes have previously been described for measurement of glycosidic activity both in cell extracts and of the purified enzyme. Among the most common fluorescent substrates for detection of galactosidase activity are β-methylumbelliferyl galactoside, resorufin galactoside, fluorescein digalactoside, and Naphthol AS-BI galactoside. Fluorescent substrates for detection of glucuronidase activity include 4-methylumbelliferyl β-D-glucuronic acid, resorufin β-D-glucuronic acid, 4-trifluoromethylumbelliferyl β-D-glucuronic acid, Naphthol AS-BI β-D-glucuronide, and fluorescein mono-β-D-glucuronide.

Most glycosidase substrates have been designed to be water soluble to facilitate their use in aqueous solution. This hydrophilic character appears to retard passage of the substrate through the membrane of living cells. Legler & Liedtke, *Glucosylceramidase from Calf Spleen*, BIOL. CHEM., 366, 1113 (1985) describe the use of fluorescent glucosidase substrates 4-heptyl-, nonyl-, and -undecylumbelliferone in assaying glucosylceramidase purified from calf spleen. Legler & Liedtke note a preference of the enzyme for long aliphatic side chains in the aglycon. The longer alkyl chains, however, appear to interfere with fluorescence and solubility in the absence of detergents. Legler & Liedtke do not use resorufin derivatives or other derivatives that have long wavelength absorption or fluorescence emission and do not discuss the assay of glucosidase inside intact living cells, or in tissues.

Although the use of fluorescent substrates is preferable to other methods, such as radioactivity, they are not entirely problem-free. In addition to the problems of cell leakage and cell entry discussed in greater detail below, some of the disadvantages of these substrates include fluorescence at a wavelength not well suited for flow cytometry (e.g. β-methylumbelliferyl galactoside, 4-trifluoromethylumbelliferyl galactoside, naphthol AS-BI galactoside), pH sensitivity or pH change necessary to exhibit maximal fluorescence (e.g. β-methylumbelliferyl galactoside), and low sensitivity or limited change in fluorescence in the presence of the enzyme (e.g. naphthol AS-BI galactoside).

U.S. Pat. No. 4,812,409 to Babb et al. (1989) discloses substrates attached to a blocked phenalenone or benzphenalenone fluorescent moiety, which when cleaved from the substrate by hydrolysis at a pH of 9 or less, releases a fluorescent moiety excitable at a wavelength above about 530 nm with maximum fluorescent emission at a wavelength of at least about 580 nm. There is no indication in the patent that the substrate is non-toxic to living cells or that the fluorescent product(s) do not leak from cells after enzymatic turnover, and are thus amenable to in vivo detection of enzyme activity.

Fluorescent compounds that are not enzyme substrates have been used to detect transformed cells. David W. Galbraith, active in research involving fluorescent dyes used with plant cells, identified four dyes used to label plant cell populations prior to gene fusion in *Selection of Somatic Hybrid Cells by Fluorescence-*

*Activated Cell Sorting*, in CELL CULTURE AND SOMATIC CELL GENETICS OF PLANTS 1, 433, ch. 50 (1984). The four dyes, octadecanoyl aminofluorescein (F18), octadecyl rhodamine B (R18), fluorescein isothiocyanate (FITC) and rhodamine isothiocyanate (RITC) were nontoxic to the cells (although FITC and RITC are toxic at high levels) and did not leak from the cells during culturing (p. 434). The fluorescein dye was added to one cell population, the rhodamine dye to the other. After gene fusion, the presence of both dyes was used to detect the heterokaryons. Galbraith noted (p. 442) that the lipophilic F18 and R18 dyes were observed localized in the membranes of cells, whereas FITC and RITC were distributed through the cytoplasm. Neither set of dyes was used to identify specific enzymes associated with the cells.

An article by Nolan, et al., *Fluorescence-activated cell analysis and sorting of viable mammalian cells based on β-D-galactosidase activity after transduction of Escherichia coli lacZ*, CELL BIOLOGY 85, 2603 (1988) describes the measurement of galactosidase activity in lacZ+ transformed cells using fluorescein di-β-D-galactopyranoside (FDG). The use of FDG to measure promoter activity is described in another article, Ikenaka, et al., *LABORATORY METHODS: Reliable Transient Promoter Assay Using Fluorescein-di-β-D-galactopyranoside Substrate*, DNA & CELL BIOL. 9, 279 (1990). FDG has excellent properties for these purposes. Despite the advantages; however, there are at least two major drawbacks that are recognized in the use of FDG and all other fluorescent substrates for the analysis and selection of transformed cells.

First, it is difficult to get the substrate through the outer cell membrane without disrupting the cell. The permeability properties of available substrates, such as 4-methyl umbelliferyl glucuronide, require detection of GUS activity in plant tissue homogenate or cell extracts. Such destructive assay conditions will certainly cause inaccuracy and set limitations when an investigator is looking for relatively rare events such as the regulation of transcription and/or translation or transformation with a chimeric gene. Nolan, et al., using FDG, reduced this problem for cells in suspension by using brief hypo-osmotic or hypotonic shock. Ikenaka, et al. used the same technique. To use hypo-osmotic shock, the cells are placed in a hypotonic solution causing the membrane to swell. Swelling of the membrane results in permeabilization of the substrate so that it enters the cell. If the cell stays too long in the dilute solution, however, it ruptures. Removal of the cells from the dilute solution must be carefully timed to maximize entry of the substrate yet minimize cell loss.

A second and more important drawback of known fluorescent substrates is the problem of cell leakage. For example, following enzymatic hydrolysis of FDG, the resulting product (fluorescein) rapidly leaks out of the cell. See, e.g., FIG. 3(c) and FIG. 4; see also, Ikenaka, et al.; Nolan, et al. Commonly half of the fluorescein leaks from the cell in about 10 minutes at about 37° C. Fluorescent products derived from other substrates, including all β-methylumbelliferyl and resorufin glycosides have been found to leak from cells under in vivo conditions even faster than fluorescein. Nolan et al., and Ikenaka, et al., working with FDG, were able to suppress the leakage of fluorescein by quickly cooling their cells to 4° C. Cooling the cells, however, also reduces the enzyme turnover rate significantly, and is not desirable when working with whole living organisms. Leakage of the fluorescent product, even at 4° C. makes enzyme activity quantitation particularly difficult. It also increases the difficulty in differentiating weakly expressing gene positive cells from the background fluorescence of negative cells.

Neither hypo-osmotic shock loading nor sudden cooling well below physiological temperatures is suitable for measuring enzyme activity in transformed living cells, tissues or organisms under physiological conditions (typically 37° C.) such as during development and cell division. A copending application, LIPOPHILIC FLUORESCENT GLYCOSIDASE SUBSTRATES (Ser. No. 07/623,600, filed Dec. 7, 1990), describes lipophilic derivatives of fluorescein glycosides and related compounds that yield green fluorescent products suitable for detection of glycosidase activity in living cells. Both classes of substrates are permeant to cells under physiological conditions, are not toxic to living cells, and are nonfluorescent until specifically hydrolyzed by the glycosidase enzyme. Both of their fluorescent products are readily detected in single cells and even within specific organelles of single cells. Substrates of either class can be selected that yield fluorescent products that are very well retained in the original cell with no or minimal leakage or transfer between marker-positive and marker-negative cells, even through cell division.

The two inventions differ, however, in the use of a different fluorophore. As a result, the compounds disclosed in the co-pending application have emission that is maximal at wavelengths less than 550 nm. The resorufin derivatives of this invention, in contrast, have orange to red emission that is maximal above 550 nm. This contrast permits, for example, the simultaneous detection of two different enzymes or a combination of activity of one enzyme and a second fluorescent label in a mixture of cells or even in a single cell. It also makes possible the detection of different genetic elements under regulation of different promoters in cells or tissues.

Hofman & Sernetz, *Immobilized Enzyme Kinetics Analyzed by Flow-Through Microfluorimetry*, ANALYTICA CHIMICA ACTA 163, 67 (1984) describes the synthesis and enzymatic properties of resorufin β-D-galactopyranoside but does not describe lipophilic alkylated derivatives of this compound or the measurement of enzyme activity inside live cells. Attempts have been made to use resorufin β-D-galactoside to detect incorporation of the lacZ gene in cells, but were unsuccessful as the result of leakage of the hydrolysis product from the cell.

Leakage of 7-hydroxyresorufin resulting from the use of 7-ethoxy- and 7-pentoxyresorufin in an assay for monooxygenase activity is described by Reiners, et al.; *Fluorescence Assay for Per-Cell Estimation of Cytochrome P-450-Dependent Monooxygenase Activities in Keratinocyte Suspensions and Cultures*, ANALYT. BIOCHEM. 188, 317 at p. 322 (1990). Leakage of metabolic products of other substrates is also described. Although Reiners, et al. note improved retention of 7-hydroxyresorufin in hepatocytes, only 29% of the intracellular product remained after 35 minutes. Furthermore, there is no indication that the activity of the enzyme they were studying (which is not a glycosidase) can be determined on a single cell basis.

U.S. Pat. No. 3,731,222 to Drexhage (1973) describes a resorufin derivative with a lower alkyl (1–6 carbons) for use as a laser dye. There is no indication in the reference that an alkylated resorufin could be attached to a carbohydrate moiety for use as a glycosidase substrate, nor that that alkyl group(s) would provide any advantage to such a substrate.

Resorufin glycosides with lower alkyl (1-5 carbons) substituents for use as glycosidase substrates are described in German Patent No. DE 3411574A1 to Klein, et al., 1985. The patent does not describe the use or the advantages of alkyl residues of more than 5 carbons to increase the time that the fluorescent hydrolysis product is retained in intact cells. In fact, the patent recites that alkyl substituents with 1-3 carbons are preferred.

SUMMARY OF THE INVENTION AND DESCRIPTION OF PREFERRED EMBODIMENTS

Figure 1:
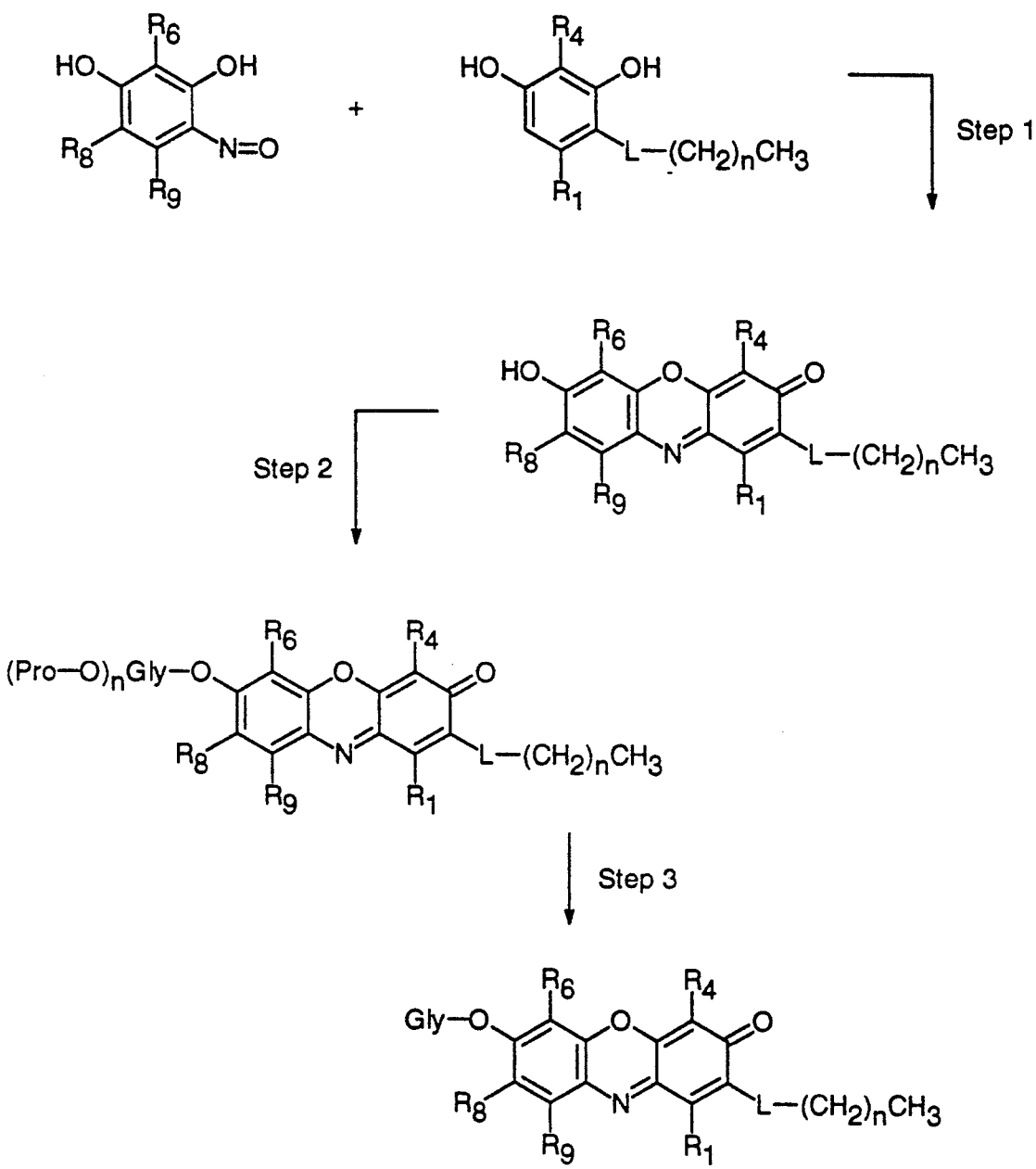
FIG. 1 is a diagram of the formation pathway of a preferred substrate. In step 1, formation of a resorufin derivative is carried out including the lipophilic group. In step 2, the fluorophore is glycosylated, and in step 3, the protecting groups are removed from the molecule to provide the final substrate.
Figure 2:
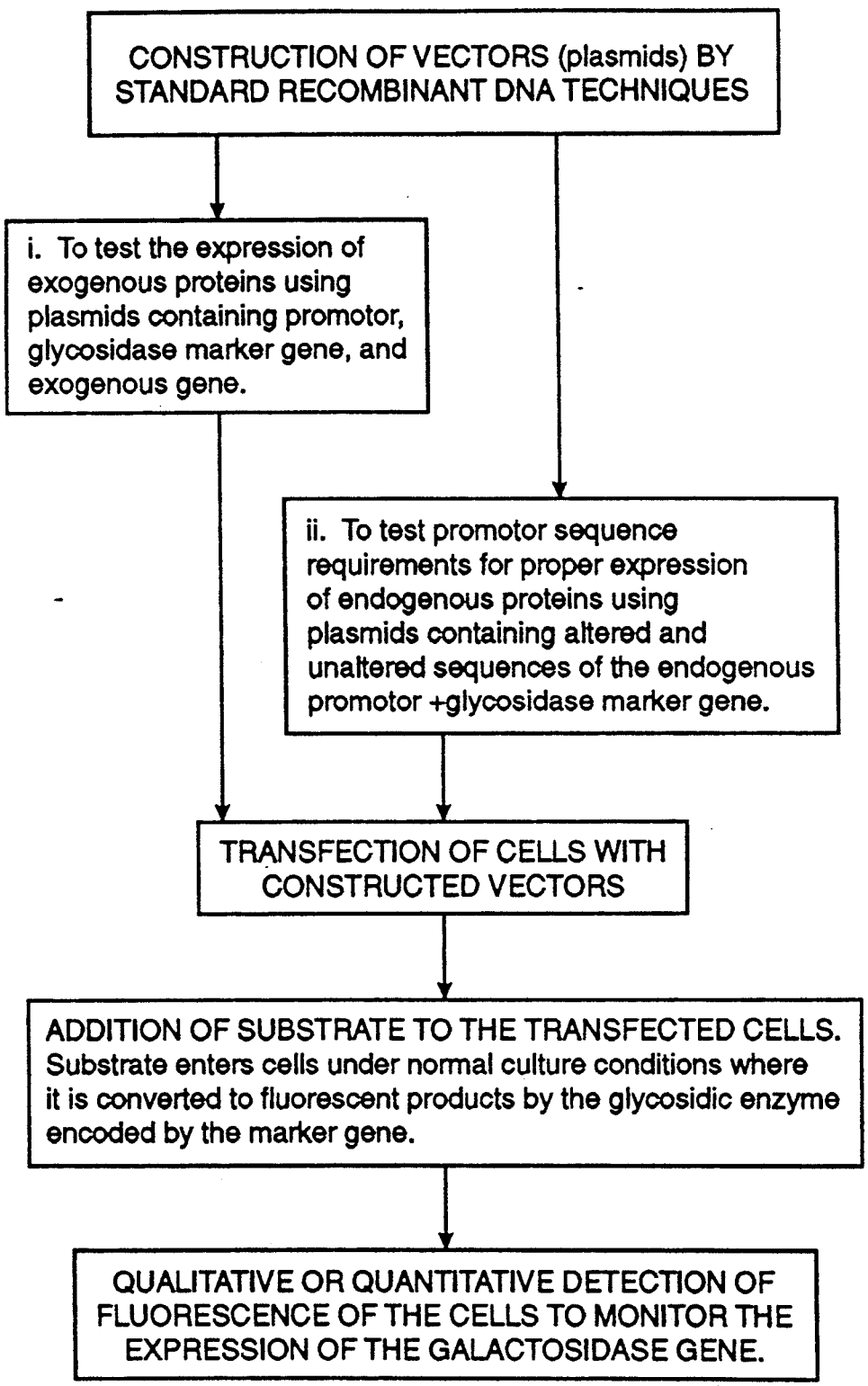
FIG. 2 is a diagram illustrating the procedure of using the substrate to detect the presence of a glycosidic enzyme resulting from gene fusion.

This invention describes a class of novel fluorogenic substrates for measuring the presence and activity of a glycosidic enzyme and whose hydrolysis products have orange to red fluorescence emission that contrasts with the green fluorescent emission of fluorescein.

The substrates are derivatives of resorufin of the general formula:

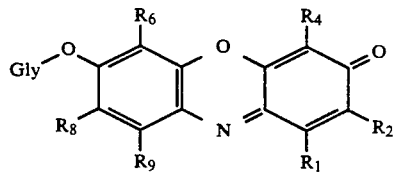

wherein Gly is a carbohydrate bonded to resorufin by a glycosidic linkage; where at least one of substituents $R_1$, $R_2$, $R_4$, $R_6$, $R_8$, and $R_9$ is a first lipophilic residue containing from about 6 to about 22 carbon atoms of the formula $-L(CH_2)_nCH_3$, where n is greater than 3 and less than 22, and where L is a methylene $-CH_2-$, an amide $-NHCO-$, sulfonamide $-NHSO_2-$, carboxyamide $-CONH-$, carboxylate ester $-COO-$, urethane $-NHCOO-$, urea $-NHCONH-$, or thiourea $-NHCSNH-$; and where the remainder of the substituents $R_1$, $R_2$, $R_4$, $R_6$, $R_8$, and $R_9$, which may be the same or different, are hydrogen, halogen, or other lipophilic residues, which may be the same or different, containing from about 1 to about 22 carbon atoms of the formula $-L'(CH_2)_mCH_3$, where m is less than 22, and where L' is methylene $-CH_2-$, an amide $-NHCO-$, sulfonamide $-NHSO_2-$, carboxyamide $-CONH-$, carboxylate ester $-COO-$, urethane $-NHCOO-$, urea $-NHCONH-$, or thiourea $-NHCSNH-$. Specifically the subject substrates contain the 7-hydroxy-3H-phenoxazin-3-one structure of resorufin in which one of the hydroxyl residues is converted to a glycoside derived from the sugar; and substituted by at least one lipophilic or hydrophobic fatty alkyl residue containing from about 6 to about 22 carbon atoms.

The two nonheterocyclic aromatic rings of the phenoxazine ring portion of resorufin may be further substituted. In one embodiment of the invention, the ring portion is substituted by one to four halogen atoms, which may be the same or different. The preferred halogens are bromine, chlorine, or iodine. The one or more halogens are substituted at the 2, 4, 6, or 8 positions, or combinations thereof.

The carbohydrate substituent (Gly) and its linkage to resorufin provide the resorufin-derived substrate with its specificity for a particular glycosidic enzyme. Gly is a hydrolyzable monovalent moiety, derived by removal of an anomeric hydroxyl group from a mono- or oligosaccharide, which is linked to the 7-oxo-position on the phenoxazine fluorophore. The linkage can be an α- or β-glycosidic linkage. The attachment of Gly to the resorufin fluorophore changes the spectral (excitation/emission) properties of the fluorophore. Typically hydrolysis of Gly by action of a specific enzyme results in a shift in the absorbance of the hydrolysis product to longer wavelengths that are not absorbed or are minimally absorbed before the removal of Gly, and an increase in fluorescence. Quantitative or qualitative detection of the hydrolysis product permits detection of the corresponding enzyme. Any of the enzymes listed in Table 1, and similar carbohydrate substrates derived from other sugars or modified sugars for which hydrolytic enzymes that hydrolyze the glycosidic linkage exist, could be detected using resorufin glycoside substrates derived from the appropriate sugar specific for the enzyme.

The first lipophilic residue, preferably an unbranched fatty alkyl residue, contains from about 6 to about 22 carbon atoms. Those substrates with the longer alkyl chain are better retained by the cell. When it is desired that the fluorescent product be strongly retained within a cell, the preferred alkyl residue contains about 12-18 carbons. Without wishing to be bound by theory, applicants believe that the hydrophobic or lipophilic residue facilitates passive diffusion of the substrate through the cell membrane and enhances retention of the fluorescent hydrolysis product, in a form where it is preferentially bound to the cell membranes rather than being free in the cellular cystosol. Binding of the product to a cell membrane considerably enhances retention of the fluorescent product by the cell and considerably reduces transfer of the resulting dye between marker positive and marker negative cells.

Preferably, each lipophilic group is directly linked to the resorufin ring, in which case L or L' is a single methylene $-CH_2-$. Alternatively, other linking groups in which the alkyl group is bonded to the resorufin through an amide $-NHCO-$, sulfonamide $-NHSO_2-$, carboxyamide $-CONH-$, carboxylate ester $-COO-$, urethane $-NHCOO-$, urea $-NHCONH-$, or thiourea $-NHCSNH-$ also result in products with similar utility where they do not materially effect the fluorescence spectra. From ease of synthesis and availability of synthetic precursors it is preferred that the first lipophilic residue is linked to the resorufin derivative at the 2 position. Attachment at other positions, however, or use of more than one lipophilic residue results in products of similar utility. Where two lipophilic residues are used, preferably the combined total length of the two alkyl chains is between 12 and 22 carbons. From ease of synthesis the two lipophilic residues are preferentially at equivalent positions on the resorufin structure, such as in the $R_2$ and $R_8$ positions.

The starting material for preparation of the lipophilic resorufin glycoside is a lipophilic resorufin ("LR"), or its respective halogenated derivative. The LR starting material commonly includes at least one lipophilic group containing from 6 to 22 carbon atoms. Most commonly, the unsymmetrical alkyl resorufin is synthesized by condensation of one mole of an appropriately substituted resorcinol with a nitrosoresorcinol (see Example 2). Alternatively, for instance, lipophilic resorufin carboxamides can be synthesized by reaction of activated resorufin carboxylic acids such as those sold by Boehringer Mannheim Corporation (Indianapolis, Ind. USA) with an aliphatic amine containing from 4 to 22 carbon atoms. Halogenation can also be accomplished subsequent to formation of the lipophilic resorufin dye such as by bromination with liquid bromine.

From the halogenated or non-halogenated LR starting material, a protected glycoside intermediate is prepared in a multi-step process. Glycosylation using a modified Koenigs-Knorr methodology involves treatment of a LR with a soft acid catalyst, an activated protected carbohydrate (APC) derivative, and a non-nucleophilic base, under anhydrous conditions. Symcollidine or quinoline are a preferred non-nucleophilic base and silver carbonate is a representative soft acid catalyst.

The APC will contain one or more sugars with an activating group at the anomeric position of the sugar to be attached to the LR. Typically the APC is a halogenated sugar, where a halogen is the activating group at the anomeric position. Depending on the reaction conditions, the sugar involved, or the anomeric isomer required, other activating groups at the anomeric position of the APC can be used, most commonly trichloroacetimidate, thiophenyl, or acetate.

Using one or more equivalents of an APC, a glycoside intermediate is formed. Because of the asymmetry typical of LR but recognizing the two resonance structures of the hydroxyphenoxazinone dye, there are two possible glycoside products. The predominant product when the lipophilic substituent ($-L(CH_2)_nCH_3$) is in the 2 position appears to be the $2-L(CH_2)_nCH_3-3$-oxo-7-O-glycoside.

After isolation of the protected glycoside intermediate, the protecting groups are removed from the protected glycoside using processes appropriate to the protecting group(s) present. For example, catalytic sodium methoxide is used for removal of acetylated alcohols, aqueous lithium hydroxide for methyl esters, etc. Final purification and crystallization yields the glycoside substrate.

Modifications of the above procedures will be obvious to a chemist skilled in the art of organic chemistry.

The substrate is useful for evaluating a glycosidic enzyme, including the evaluation of a variety of detection, localization, monitoring, and quantitative parameters. The substrate provides the desired permeability, retention, detectability, specificity and lack of toxicity to detect activity of a particular gene in single cells containing the gene, by detecting the enzyme activity that results from the presence of the gene. In combination with a compound or compounds having an emission maximum that is less than 550 nm, the resorufin derivatives of this invention having an emission maximum that is greater than 550 nm can be used to simultaneously detect two different enzymes in a mixture of cells or even in a single cell. These characteristics permit analysis, sorting and cloning of the cells and monitoring of cell development in vitro and in vivo.

To detect the presence of a glycosidic enzyme or enzymes in a substance, a substrate is selected that is specific for the enzyme to be detected. The sugar of the carbohydrate substituent and its linkage to resorufin provides the substrate with specificity for the particular glycosidic enzyme. The substrate comprising the sugar specific for the enzyme appropriately linked to the lipophilic resorufin derivative is combined with the substance being evaluated.

The substrates are particularly effective in detecting glycosidic enzyme activity inside a living cell. The fluorescent enzymatic hydrolysis products are specifically formed and adequately retained inside living cells, and are nontoxic to the cells. Furthermore, the substrates can penetrate the cell membrane under physiological conditions. Increasing the lipophilicity of the fluorescent product by addition of extra methylene groups improves the product retention while decreasing the number of methylene groups accelerates the rate of product clearance from the cell.

To detect the presence of the glycosidic enzyme in living cells, the substrate is added to the standard culture medium of the cells being evaluated. If the cells being evaluated have been subjected to transformation or other disruptive procedures, the cells should be allowed to stabilize before adding the fluorescent substrate. Typically 12-24 hours rest is sufficient for the cells to stabilize. For adherent cells, growing them on several cover glasses inside a Petri dish will enable cell samples to be taken out at any designated time during the incubation for examination.

For ease of addition to the culture medium, the substrate is dissolved in solution to make a labeling reagent. Preferably the substrate is dissolved in a polar, aprotic organic solvent sufficiently dilute not to disrupt cell membrane structure when the labeling reagent is added to the culture medium. A 10 mM solution of substrate in 20% DMSO yields an effective stock solution of the labeling reagent that remains stable for at least a month if stored 4° C. in the absence of light.

The labeling reagent is added to culture medium of the cells being evaluated so that the cells incubate further in a labeling culture medium. Some plant cells may only be penetrable as protoplasts, i.e. after alteration or removal of the outer membrane. The labeling reagent is added to the culture medium in an amount sufficient to yield a concentration of about 50 to about 250 $\mu$M of substrate, preferably about 100 to about 200 $\mu$M of substrate, in the labeling culture medium. A sterilized labeling reagent is preferred so that the substrate will be taken up by cells in a normal physiological condition during their growth. Usually the labeling reagent is first added to fresh culture medium to form a fresh labeling culture medium. The fresh labeling culture medium is then filter-sterilized by passing through a low protein-binding, sterilizing filter, such as a 0.20 $\mu$m pore size ACRODISC TM filter. Spent culture medium is removed and sterilized fresh labeling medium is added to culturing cells.

The cells are incubated in the labeling culture medium for sufficient time for the substrate to enter the cells and to react with the enzyme to yield a fluorescent detection product. Commonly this time is about 1-10 hours. A sample of the cells is observed under a microscope equipped with a filter for visualizing fluorescence. Preferably, the sample of cells is exposed to a radiation source at a wavelength of between about 488 and about 550 nm and the emission is detected beyond 550 nm. Washing the cell sample with normal culture medium before examination will reduce background fluorescence from broken cells or decomposed substrate.

The fluorescent detection product is only observed inside cells producing the specific glycosidic enzyme. The substrates can be used to detect activity of the enzyme in any medium, cell-free or not, that contains the enzyme. The glycosidase enzyme being evaluated inside cells may be present endogenously, or present as a result of manipulation of the cell's genome, such as by transformation. In one embodiment of the invention, the presence of the fluorescent detection product is used to indicate the successful insertion of foreign genetic material responsible for the production of the enzyme. In another embodiment of the invention, the substrates are used to monitor whether and to what extent a glycosidic enzyme has been successfully affected by promoters and/or repressors for the enzyme. In such embodiments involving evaluation of genetic information, appropriate cells are selected for incubation with a suitable substrate specific for the enzyme useful to evaluate such genetic information. Appropriate cells are selected or prepared by means generally known in the art. In the case of evaluating the response of an enzyme with respect to an inducible promoter, the appropriate inducer is subsequently added to the incubated cells.

Regulation of gene expression by inducible upstream elements can be evaluated using a suitable reporter gene and a substrate specific for the product of the reporter gene. Cells containing appropriate genetic material useful for the evaluation of such regulation are selected or prepared according to methods known in the art (Emilie, Peuchmaur, Barad, Jouin, Maillot, Couez, Nicolas, Malissen, EUR. J. IMMUNOL. 19, 1619 (1989) incorporated herein by reference). In yeast, genes that are expressed in a cell-type specific manner and genes whose transcription increases in response to peptide mating pheromones are known. Expression levels of such controlled genes can be related to substrate turnover levels by using lacZ as a reporter gene. The general procedure involves fusing the gene of interest adjacent to the reporter gene and using this construct, usually on a replicating plasmid, in transformation of selected cells. After appropriate growth of the selected cells, the cells are assayed for glycosidase activity using the substrates. The level of activity can be analyzed by fluorescence microscopy or video-fluorescence image analysis at the single cell level by methods known in the art, such as described in Jarvis, et al., MOLEC. & CELL. BIOL. 8, 309 (1988), incorporated herein by reference. Detection of such induction is facilitated by the improved cell retention properties of the lipophilic galactosidase substrates.

For example, yeast promoters are made up of two components: (1) an upstream activation sequence (UAS) that confers the characteristic regulatory pattern of the gene and (2) a TATA sequence. The full length of UAS will drive a high level of transcription of genes encoded downstream. It is possible to examine whether the complete sequence of the UAS gene is important for the regulation of the transcription of downstream elements. Due to the manipulation of the promotor sequence, different levels of expression of the lacZ gene in each recombinant yeast strain will result in varied β-galactosidase activities in the transformed yeast cells.

Alternatively, the substrate can be used to evaluate an enzyme added to cells exogenously, for example, by a glycosidase enzyme covalently bound to a protein such as an antibody to form an enzyme-protein complex, usually as an enzyme conjugate, that binds to or enters the cell. The cells are incubated in a complex-containing medium. The incubated cells are subsequently washed and transferred to a labeling medium containing substrate specific for the enzyme. After incubating the cells in the labeling medium sufficiently long for the substrate to enter the cells, a portion of the cells is evaluated for fluorescence as above. The presence or absence of a fluorescent detection product is used to determine whether or not the conjugate or complex has bound to or entered the cells. Enzymatic generation of the fluorescence through use of a glycosidase conjugate of, for instance, an antibody to a cell surface receptor, provides a means of obtaining amplification of the fluorescence signal beyond that normally obtained using direct conjugates of fluorescence dyes with an antibody or protein that binds to or enters the cell.

Because of the production of a unique reddish fluorescence, the substrate can be used in conjunction with another substrate of a dye with a different color fluorescence yielding a multicolor system for evaluating two different analytes. For such an evaluation of two different enzymes present in a sample, the sample is combined with 1) the novel resorufin substrate specific for one of the enzymes of interest and having an emission maximum greater than about 550 nm; and 2) a second substrate specific for a different enzyme having an emission maximum less than about 550 nm. Where the sample is living cells, the second substrate should be equally well-retained in and nontoxic to such cells, preferably the substrate described in the co-pending application LIPOPHILIC FLUORESCENT GLYCOSIDASE SUBSTRATES (U.S. Ser. No. 07/623,600, filed Dec. 7, 1990) (incorporated herein by reference). After a sufficient period for reaction of both substrates, the cells are washed to remove fluorescent decomposition products and analyzed using a suitable instrument such as a microscope or flow cytometer commonly employing optical filters to separate the two colors of fluorescence.

The invention can be used to sort cells according to their glycosidic enzyme activity. As the substrates generate fluorescence products that are well cell-retained upon the action of glycosidic enzyme inside cells, an easy and convenient selection/collection of gene-transferred cells of interest is available through a fluorescence-activated cell sorting (FACS) technique. In principle, the substrates are loaded into a cell and then converted to fluorescent products to an extent determined by the glycosidic enzyme activity (or amount) inside the cell. It has been demonstrated (e.g. Nolan, et al.) that modern flow cytometers can sort the cells by their fluorescence signal amplitude therein and, in turn, by cell enzyme activity.

For the sorting of a cell being investigated, the cell is loaded with the glycosidase substrate and incubated to obtain a sufficient fluorescence signal which corresponds to the cell glycosidic enzyme activity being evaluated. The procedure for cell staining under physiological conditions has been described above. To discriminate cells expressing low enzyme activity from cells that express high levels of enzyme activity, it is preferred to limit the period of incubation to the minimum necessary to achieve the desired resolution. The appropriate balance between sufficient and excessive fluorescence development varies with the substrate concentration, the cell type in terms of membrane permeability for both the substrate and the hydrolysis product, and the distribution of enzyme activity in cell organelles. In a mammalian cell that contains a glycosidic enzyme, 30 to 60 minute incubation rather than hours or overnight, is recommended when a substrate concentration of 10 to 50 μM is used to stain the cell. Other known automated methods of cell sorting may also be used. There is extensive literature published on cell analysis and sorting instrumentation for flow cytometry. Post-sorting cell examination by other techniques such as assay of enzyme activity or cytochemistry may be needed to confirm the sorting results or to confirm the success of the sorting.

The labeling reagent shows no detectible cytotoxicity. Cells incubated with $C_{12}$-Resorufin-Gal (100 μM) in the culture medium exhibited equivalent population doubling time as in controls. Cells preincubated in the labeled culture medium for 24 hours could be subcultured and the cells of the second generation were normal. The cells grown in $C_{12}$-Resorufin-Gal (100 μM) for 4 days had normal morphology and remained viable.

Transfer of dye between cells was tested in a semiconfluent mixture of enzyme expressing (lacZ+) and nonexpressing (lacZ−) cells. Visualization of adjacent (visible morphological contacts formed) fluorescent and nonfluorescent cells indicated that the fluorescent dye did not transfer between cells.

The following examples are included by way of illustration and not by way of limitation.

EXAMPLE 1

Preparation of Resorcinol Containing an 18-carbon Alkyl Chain at the 4-position

The following compound was prepared:

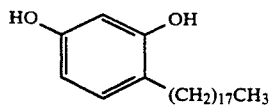

Preparation of 4-octadecanoylresorcinol

Stearic acid (200 g, 0.70 mole) is dissolved in boron trifluoride etherate (275 mL). Resorcinol (100 g, 0.91 mole) is added as a solution in $BF_3$ etherate (75 mL) and this mixture is heated to reflux with stirring for 4 hours. The solution is cooled to room temperature, diluted with $CHCl_3$ (300 mL) and poured into water (700 mL at 0° C.). The organic layer is separated and washed with saturated sodium chloride solution (1×200 mL), dried over anhydrous $Na_2SO_4$, filtered and evaporated under reduced pressure. This residue is crystallized from hexanes (300 mL) and then recrystallized from ethanol (300 mL) to yield 15.8 g tan crystals. 1H NMR (DMSO-$d_6$) δ:0.87(t,3H); 1.22(m,28H); 1.62(m,2H); 2.86(t,2H); 3.82(s,2H); 6.22(d,1H); 6.33(dd,1H); 7.67(d,1H). m.p.=78° C.; $SiO_2$-t.l.c. (2:8 EtOAc:$CHCl_3$) $R_f$=0.88

Preparation of 4-octadecylresorcinol

Stearoylresorcinol (0.32 g, 0.85 mmole) and anhydrous hydrazine (0.25 mL) are combined in diethylene glycol (20 mL). After the stearoylresorcinol dissolves, potassium hydroxide pellets (0.1 g, 1.78 mmole) are added, and the solution is refluxed at 100° C. for 1 hour (the presence of the hydrazone is confirmed by $SiO_2$ t.l.c. ($R_f$=0.45, 9:1 $CHCl_3$:MeOH), with $H_2O$ removed through use of Dean-Stark type distillation until the temperature reaches 115° C. The temperature is then elevated to 180°-190° C. for an additional 3 hours. The resulting diethylene glycol solution is cooled to room temperature, acidified using 0.5M $H_2SO_4$ solution (approx. 8 mL, to pH 2-3), diluted with water (250 mL), and the aqueous solution is extracted with ethyl acetate (3×100 mL). The combined ethyl acetate layers are washed with water (2×100 mL) and saturated NaCl solution (1×100 mL) and dried over anhydrous $Na_2SO_4$.

The organic layer is evaporated under reduced pressure and dried in vacuo to give an off-white powder (230 mg, 74%). $^1H$ NMR ($CDCl_3$) δ:6.97(d,1H); 6.33(dd,1H); 6.31(d,1H); 4.65(s,1H); 4.57(s,1H); 2.50(t,2H); 1.56(m,2H); 1.24(br s,30H); 0.88(t,3H). m.p.=98°-101° C. $SiO_2$-t.l.c. 1:9 MeOH:$CHCl_3$) $R_f$=0.30.

EXAMPLE 2

Preparation of a Resorufin Containing a Twelve Carbon Fatty Alkyl Chain at the 2-position The following compound was prepared:

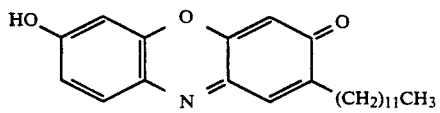

Preparation of 2-dodecyl-7-hydroxy-3H-phenoxazine-3-one ("dodecylresorufin")

A solution of 4-dodecylresorcinol (8.5 g, 30.53 mmole) (Aldrich Chemical Company) and 4-nitrosoresorcinol (5.0 g, 35.9 mmole) (Aldrich) in concentrated sulfuric acid (100 mL) is heated to 67° C. with stirring for 5 hours. The reaction mixture is allowed to cool to room temperature, poured into ice-water (1800 mL) and filtered. The resulting precipitate is washed with water until the filtrate is neutral to pH paper. This precipitate is dissolved in chloroform and the combined aqueous filtrates are back-extracted with chloroform (6×250 mL) to recover additional product. The combined chloroform layers are dried over anhydrous sodium sulfate and evaporated to a dark purple solid (2.55 g), homogenous by $SiO_2$-t.l.c. (45:5:1 chloroform:methanol:triethylamine) $R_f$=0.69. An additional 5.58 g of product is obtained by neutralization of the aqueous filtrates above with 8M KOH and extraction with chloroform (total yield=8.13 g, 68%). $^1H$ NMR ($d_6$-DMSO) δ:7.57(d,1H); 7.27(s,1H); 6.79(D,1H); 6.66(s,1H); 6.23(s,1H); 4.14(c,1H); 2.46(t,2H); 1.52(c,2H); 1.23(c,18H); 0.85(c,3H).

EXAMPLE 3

Preparation of a Substrate Having a Galactopyanoside Blocking Group at the 8-position and a Eighteen Carbon Alkyl Chain at the 2-position of Resorufin The following compound was prepared:

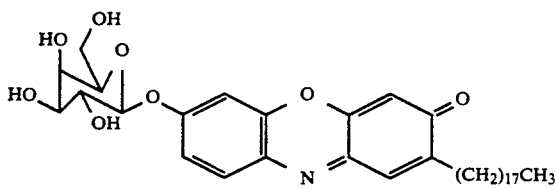

Preparation of 2-octadecyl-7-(2,3,4,6-tetra-O-acetyl β-D-galactopyranosyloxy)-3H-phenoxazin-3-one A mixture of 7-hydroxy-2-octadecyl-3H-phenoxazine-3-one ("octadecylresorufin") (220 mg, 0.47 mmole), powdered, activated 4Å molecular sieves (0.5 g), sym-collidine (125 μL, 0.95 mmole), and silver carbonate (155 mg, 0.56 mmole) in dry dichloromethane (20 mL) is allowed to stir at room temperature, under an atmosphere of dry nitrogen gas, in the dark for 1 hour. To this mixture is added 1-bromo-2,3,4,6-tetra-O-acetyl-α-D-galactopyranoside (389 mg, 0.95 mmole), slowly with stirring, and the resulting heterogenous solution allowed to stir as above for 72 hours. After this time the reaction mixture is filtered through a pad of diatomaceous earth. The precipitate is washed with chloroform (5×10 mL) and the combined organic filtrates are extracted with 1M aqueous HCl (1×75 mL), saturated aqueous sodium bicarbonate solution (1×75 mL), 1M sodium thiosulfate (1×75 mL), and water (1×75 mL). The organic layer is dried over anhydrous sodium sulfate, filtered, evaporated under reduced pressure, and dried in vacuo to an orange-brown powder (440 mg). An analytical sample of the title compound can be isolated by preparative t.l.c. (20×20 cm $SiO_2$ plate; eluent=9:1 chloroform:ethylacetate) with the bright-orange product eluting at the highest $R_f$(0.44), (50 mg from 200 mg applied).

Preparation of 2-octadecyl-7-(β-D-galactopyranosyloxy)-3H-phenoxazin-3-one ($C_{18}$-Resorufin-Gal)

A suspension of dry 2-octadecyl-7-(2,3,4,6-tetra-O-acetyl β-D-galactopyranosyloxy)-3H-phenoxazin-3-one (50 mg, 0.06 mmole) in anhydrous methanol (40 mL) is cooled to 0° C. in an ice-bath while under an atmosphere of dry nitrogen gas. A solution of freshly prepared sodium methoxide in methanol is added (200 μL, 1.13M solution) and this mixture is allowed to stir at 0° C. for 2 hours then at ambient temperature for 3 hours. The red product is filtered and washed with methanol. The resulting red-orange solid is dried in vacuo (28 mg, 71%). The filtrate is neutralized with Amberlite IRC 50(H+) resin (pH 4) and filtered, with the resin being washed with methanol (5×10 mL). The combined filtrates are evaporated to dryness and dried in vacuo to yield a second crop of product (8 mg, 91% total) T.l.c. ($SiO_2$) (8:2 ethyl acetate:methanol) $R_f$=0.33. $^1$H-n.m.r.($d_6$-DMSO) δ:7.77(d,1H); 7.30(s,1H); 7.13(s,1H); 7.10(d,1H); 6.27(s,1H); 5.02(d,1H,H−1); 3.72(d,1H); 3.70–3.25(m,5H); 2.48(t,2H); 1.52(m,2H); 1.26(m,30H); 0.86(t,3H).

EXAMPLE 4

Preparation of a Substrate Containing a Twelve Carbon Fatty Alkyl Chain at the 2-position and a β-D-glucuronic Acid at the 7-position of Resorufin The following compound was prepared:

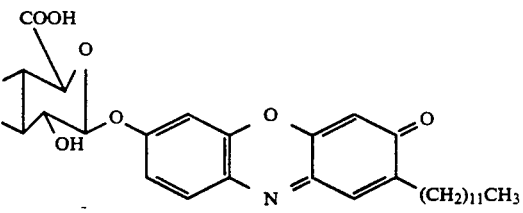

Preparation of the protected glucuronide of dodecyl resorufin 2-dodecyl-7-hydroxy-3H-phenoxazine-3-one (2.0 g, 5.2 mmole) is dissolved in quinoline (50 mL), containing anhydrous $CaSO_4$ powder (5 g), silver carbonate (2.86 g, 10 mmole) and 1-bromo-2,3,4-tri-O-acetyl α-D-glucopyranuronic acid, methyl ester (4.20 g, 10 mmole). This mixture is stirred under anhydrous conditions in the dark at ambient temperature for 72 hours. The reaction solution is filtered through a pad of diatomaceous earth and the filter bed is washed with ethyl acetate (200 mL). The ethyl acetate solution is back-extracted with cold 3M hydrochloric acid (1×200 mL, 0° C.) followed by saturated sodium bicarbonate solution (4×200 mL) and water (4×100 mL) until very little red color appears in the aqueous layer. The solution is dried over anhydrous sodium sulphate, evaporated, and dried in vacuo (3.36 g). The crude product is purified by silica gel column chromatography using 1% methanol in toluene as eluent to give a dark red wax (0.63 g, 17%).

Preparation of 2-dodecylresorufin glucuronide methyl ester

The protected dodecyl resorufin glucuronide above (0.63 g, 0.89 mmole) is suspended in anhydrous MeOH (60 mL) and this mixture is stirred under dry nitrogen at 0° C. while sodium methoxide/methanol solution is added (0.50 mL of a 0.99M solution). The pH is maintained between 8 and 9 by adding more NaOMe/MeOH solution as needed. This solution is stirred for 4 hours, neutralized to pH 5 using washed, dry Amberlite IRC 50 (H+) ion exchange resin, filtered, evaporated and dried in vacuo.

Preparation of 2-dodecylresorufin β-d-glucuronide ($C_{12}$-Resorufin GlcU)

The above crude sample of the above 2-dodecylresorufin glucuronide methyl ester is dissolved in a 5:1 acetonitrile:dichloromethane solution (4 mL). A freshly prepared lithium hydroxide solution (10.2 mL of a 0.08M solution) is added slowly to the flask and stirring is continued at 0° C. for 30 minutes and at room temperature for 2 hours. The solution is neutralized using Amberlite IRC 50 (H+) ion exchange resin, filtered and evaporated to a dark red oil which is purified on by reverse-phase column chromatography on Sephadex ™ LH-20 prepared in and eluted with water to give 206 mg of the pure free acid (0.359 mmoles, 40% from the fully protected material). m.p.>250° C. (d): $SiO_2$-t.l.c. (7:1:1:1 ethyl acetate:methanol:water:acetic acid); $R_f$=0.46.

EXAMPLE 5

Labeling of LacZ+Cells with the Fluorogenic Substrate 2-Dodecyl-7-($\beta$-D-Galactopyranosyloxy)-3H-Phenoxazin-3-One ($C_{12}$-Resorufin-Gal)

CRE BAG 2 (lacZ+) cells were used to test the effectiveness of the substrate in labeling lacZ+ cells. NIH 3T3 (lacZ−) cells were used as a control. Both cell lines were obtained from American Type Culture Collection Co., Rockville, Md. The cells were grown in a humidified atmosphere of 5% $CO_2$ in Dulbecco's modified Eagle's medium (DMEM) supplemented with 10% calf serum, 50 μg/mL gentamycin, 300 μg/mL L-glutamine and 10 mM HEPES pH 7.4 (culture medium).

Stock solution of labeling reagent $C_{12}$ Resorufin-Gal is dissolved in 20% DMSO to get 20 mM stock solution. Stock solution should be kept sealed a in brown reagent bottle and stored at −20° C.

Labeling culture medium

Labeling reagent is added to fresh culture medium in an amount sufficient to make 100 μM $C_{12}$-Resorufin-Gal labeling culture medium. Labeling culture medium is filter-sterilized by passing through an ACRODISC TM filter (0.20μ pore size).

Examination of cells

Cells were washed with fresh (nonlabeling) culture medium before examination. Cells are observed using a microscope equipped with a filter optimized for tetramethylrhodamine which has absorption and emission similar to those of resorufin. At 100 μM concentration, after about 30 minutes incubation, fluorescence is observed inside CRE BAG 2 cells but not in 3T3 cells. After about 2-4 hours, the fluorescence intensity in CRE BAG 2 cells reaches its highest level.

EXAMPLE 6

Analysis and Sorting of LacZ− and LacZ+ Cells by Facs Using Glycosidic Substrates The mixture of cells used for analysis and sorting (if desired) is a mixture of about 50–99% NIH3T3 (lacZ−) cells and about 1–50% CRE BAG 2 (lacZ+) cells. The cell source, culturing and substrate labeling procedure are essentially same as EXAMPLE #5: LABELING OF LacZ+ CELLS WITH THE FLUOROGENIC SUBSTRATE. For positive/negative sorting, the substrate is incubated with cells for 5 to 6 hours to achieve a maximum cell fluorescence. For subclone analysis and sorting of CRE BAG 2 cells, the substrate incubation is limited to between 30–60 minutes to facilitate discrimination of low activity and high activity cells.

Flow Cytometer Instrumentation

Suitable instrumentation for simultaneous analysis and sorting of lacZ+ cells includes a FACS II TM cell sorter (Becton and Dickinson, Sunnyvale, Calif.). This instrument is typically equipped with an argon ion laser (488 nm, Mountain View, Calif.) and a 70 μM nozzle. Cell autofluorescence is compensated by means of a two-color system. The typical cell velocity for sorting is 1000-2000 cells/second. Preferably the cell culture medium without substrate serves as the sheath fluid. The fluorescence of lacZ− cells and lacZ+ cells is typically separated by at least a 10 fold difference in intensities.

Cell Collection and Examination

The sorted cells are collected in a 96 well microtiter plate (Corning, N.Y.). The cell galactosidase activity is examined by means of the permeant fluorogenic substrate resorufin galactoside (Molecular Probes, Inc., Eugene, Oreg.). To a 20 μL cell sample in a microliter well, is added 200 μL of a 0.5 mM resorufin galactoside solution in 0.1M phosphate buffer containing 1 mM $MgCl_2$ and 0.1% Triton X-100. After 1 hour incubation, the plate is read in a CYTOFLUOR TM fluorescence plate reader (Millipore, Bedford, Mass.) with excitation at 560 nm, emission at 645 nm, sensitivity=1. A fluorescence reading below 20 can be scored lacZ− cell and a reading higher than 60 can be scored lacZ+. The resorufin galactoside can detect the enzyme activity in a single lacZ+ cell within 1 hour.

EXAMPLE 7

Detection of Gus Gene Expression in Transformed Plant Cells with $C_{12}$-Resorufin Glucuronide In our cellular assay, tobacco plants with and without the GUS gene (CaMV35S-GUS, cauliflower mosaic virus 35S promoter with the coding region of GUS) are used. (Ref: Jefferson, R. A., EMBO J., 1987, 6, 3901–3907).

Sections of the stem of both plants are cultured on Murashige and Skoog basal medium with sucrose and agar inside of plant culture dish at 2000 lux, 18 h day, 26° C. The calli are collected from the dishes, cut to small pieces and transferred to liquid medium (in screw cap 50 mL Erlenmeyer flasks) to get a cell suspension that is shaken at 120 rpm in a culture room. Filtration sterilized 1 mM $C_{12}$-Resorufin-GlcU solution (in water) is added to the cell suspension to a final concentration of 100 μM. After incubating cells in normal conditions for 4 hours, 1 mL of the suspension is spun down to obtain the cells for analysis. The cells are resuspended in 100 μL of fresh culture medium, placed onto a glass slide, covered with a cover glass and sealed with wax.

Both the GUS+ and control tobacco cells are examined under a Ziess microscope equipped with a rhodamine filter set. Photographs can be taken of both fluorescent and Nomarski images (Fujichrome P1600D, color reversal film, daylight). Only the GUS gene positive tobacco plant cells are stained with $C_{12}$-Resorufin-GlcU and show bright orange red fluorescence that is most evident in the cell membrane.

EXAMPLE 8

Detecting the Induction of Two Different Promoters, A and B, During the Cell Cycle by Using Two Fluorogenic Substrates.

1. Transformation

A fibroblast cell line, such as NIH/3T3 cell, is co-transformed with two plasmids: #1 and #2. Plasmid #1 is constructed with an upstream promoter A that drives a high level expression of lacZ gene ($\beta$-galactosidase). Plasmid #2 is constructed with an upstream promoter B that drives a high level expression of GUS gene ($\beta$-glucuronidase). Promoters are selected so that promoter A will only be induced by a specific $\alpha$-molecule existing in the $G_1$ phase and promoter B will be induced by a specific $\beta$-molecule existing in $G_2$ phase.

2. Simultaneous staining with two substrates

The transformed cells are incubated with two lipophilic, fluorogenic substrates $C_{12}FDG$ (ImaGene Green TM, Molecular Probes, Eugene, Oreg.) and $C_{12}$-Resorufin-GlcU (50 mM each) under normal culture conditions for 30 minutes. The cells are then washed and processed for microscopic examination under a Zeiss microscope equipped with both FITC (EX 485 nm/EM 530 nm band pass filter) and rhodamine (EX 540 nm/EM 590 nm) filter sets.

3. Results

. The cells in G1 phase show green fluorescence (with the FITC filter set) and those in G2 phase show red fluorescence (with the rhodamine filter set). After a longer incubation time, such as 8 hours, a lot of cells will show yellow fluorescence (i.e. a mixture of green and red fluorescence).

It is to be understood that, while the foregoing invention has been described in detail by way of illustration and example, numerous modifications, substitutions, and alterations are possible without departing from the spirit and scope of the invention as described in the following claims.

What is claimed is:

1. A glycosidase substrate comprising a resorufin derivative of the formula:

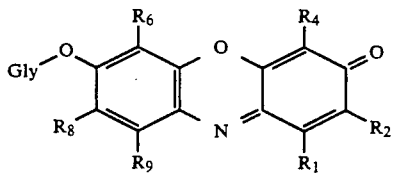

wherein Gly is a carbohydrate bonded through an anomeric carbon atom to the derivative in a glycosidic linkage;
where at least one of substituents $R_1$, $R_2$, $R_4$, $R_6$, $R_8$, and $R_9$ is a first lipophilic residue of the formula $—L(CH_2)_nCH_3$, where n is greater than 3 and less than 22, and where L is a methylene $—CH_2—$, an amide $—NHCO—$, sulfonamide $—NHSO_2—$, carboxyamide $—CONH—$, carboxylate ester $—COO—$, urethane $—NHCOO—$, urea $—NHCONH—$, or thiourea $—NHCSNH—$; and
where the remainder of substituents $R_1$, $R_2$, $R_4$, $R_6$, $R_8$, and $R_9$ which may be the same or different, are hydrogen, halogen, or other lipophilic residues, which may be the same or different, containing from about 1 to about 22 carbon atoms of the formula $—L'(CH_2)_mCH_3$, where m is less than 22, and where L' is a methylene $—CH_2—$, an amide $—NHCO—$, sulfonamide $—NHSO_2—$, carboxyamide $—CONH—$, carboxylate ester $—COO—$, urethane $—NHCOO—$, urea $—NHCONH—$, or thiourea $—NHCSNH—$.

2. A substrate, as claimed in claim 1, wherein Gly is a monosaccharide.

3. A substrate, as claimed in claim 1, wherein Gly is a sialic acid, a glucose, galactose, galactose, mannose, fructose, glucosamine, glucuronic acid, fucose, rhamnose, galactosamine, an arabinose, iduronic acid, or a cellobiose.

4. A substrate, as claimed in claim 3, wherein the Gly is a galactose, a glucuronic acid, or a cellobiose.

5. A substrate, as claimed in claim 4, wherein Gly is linked to the resorufin derivative in a β-glycosidic linkage through an anomeric carbon atom of said carbohydrate.

6. a substrate, as claimed in claim 5, wherein Gly is β-D-galactose.

7. A substrate, as claimed in claim 5, wherein Gly is β-D-glucuronic acid.

8. A substrate, as claimed in claim 5, wherein Gly is β-D-glucose.

9. A substrate, as claimed in claim 5, wherein Gly is β-cellobiose.

10. A substrate, as claimed in claim 1, wherein L is methylene $—CH_2—$, amide $—NHCO—$, or carboxamide $—CONH—$.

11. A substrate, as claimed in claim 10, wherein L is methylene.

12. A substrate, as claimed in claim 1, wherein $R_2$ is the lipophilic residue and n is less than 11.

13. A substrate, as claimed in claim 1, wherein $R_2$ is the lipophilic residue and n is greater than 9 and less than about 18.

14. A substrate, as claimed in claim 13, wherein 1-3 of substituents $R_4$, $R_6$, and $R_8$ are halogens, which may be the same or different.

15. A substrate, as claimed in claim 1, wherein
Gly is β-D-galactose, β-D-glucuronic acid, β-D-glucose, or β-cellobiose;
$R_2$ is an lipophilic residue $—L(CH_2)_nCH_3$, where n is greater than 8 and less than 18, and L is methylene $—CH_2—$, amide $—NHCO—$, urethane $—NHCOO—$, urea $—NHCONH—$, thiourea $—NHCSNH—$, or sulfonamide $—NHSO_2—$.

16. A substrate, as claimed in claim 15, wherein $R_2$ is $—L(CH_2)_{10}CH_3$, and L is alkyl $—CH_2—$, amide $—NHCO—$, or carboxamide $—CONH—$.

17. A nonfluorescent resorufin substrate specifically hydrolyzable by a glycosidase inside a cell to yield, after greater than about 2 minutes, a fluorescent resorufin detection product excitable at between about 460 nm and 570 nm and with fluorescence emission maximum at a wavelength longer than about 550 nm, which fluorescent detection product is retained inside a viable cell more than about 2 hours at greater than about 15° C. and which is non-toxic to the cell.

18. A method for evaluating a glycosidic enzyme in a sample comprising:
a) contacting the sample to be evaluated with a non-fluorescent resorufin substrate of the formula

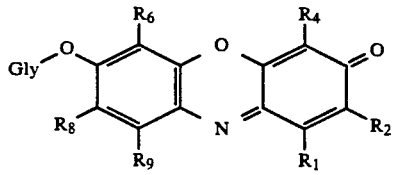

wherein Gly is a carbohydrate attached through its anomeric carbon in a glycosidic linkage that is specifically hydrolyzable by said enzyme to yield a fluorescent phenoxazine analog;
where at least one of substituents $R_1$, $R_2$, $R_4$, $R_6$, $R_8$, and $R_9$ is a first lipophilic residue of the formula $—L(CH_2)_nCH_3$, where n is greater than 3 and less than 22, and where L is a methylene $—CH_2—$, an amide $—NHCO—$, sulfonamide $—NHSO_2—$, carboxamide $—CONH—$, carboxylate ester $—COO—$, urethane —NHCOO—, urea —NHCONH—, or thiourea —NHCSNH—; and where the remainder of substituents $R_1$, $R_2$, $R_4$, $R_6$, $R_8$, and $R_9$ which may be the same or different, are hydrogen, halogen, or other lipophilic residues, which may be the same or different, containing from about 1 to about 22 carbon atoms of the formula —L'(CH$_2$)$_m$CH$_3$, where m is less than 22, and where L' is a methylene —CH$_2$—, an amide —NHCO—, sulfonamide —NHSO$_2$—, carboxamide —CONH—, carboxylate ester —COO—, urethane —NHCOO—, urea —NHCONH—, or thiourea —NHCSNH—;

b) removing a first portion of said sample;

c) exciting said first portion of the sample with a radiation source at a wavelength of between about 460 nm and about 570 nm; and d) observing the first portion in conjunction with means for the detecting fluorescence intensity of the fluorescent analog.

19. A method, as claimed in claim 18, for evaluating a glycosidic enzyme in living cells and wherein contacting the sample with the substrate comprises incubating the cells in a medium containing said substrate for sufficient time, such that the substrate enters the cells.

20. A method, as claimed in claim 19, for evaluating two glycosidic enzymes, wherein the incubation of cells in a medium containing said substrate further comprises adding a substrate that yields a separately detectable fluorescent reaction product, and incubating for sufficient time, such that both substrates enter the cells.

* * * * *